United States Patent [19]

McGeehin

[11] Patent Number: 5,856,780
[45] Date of Patent: Jan. 5, 1999

[54] SEMICONDUCTOR SENSORS AND METHOD FOR DETECTING FIRES USING SUCH SENSORS

[75] Inventor: Peter McGeehin, Compton, England

[73] Assignee: Capteur Sensors & Analysers, Ltd., United Kingdom

[21] Appl. No.: 755,285

[22] Filed: Nov. 22, 1996

Related U.S. Application Data

[63] Continuation-in-part of Ser. No. 232,017, filed as PCT/GB92/01964, Oct. 26, 1992, abandoned.

[30] Foreign Application Priority Data

Oct. 24, 1991 [GB] United Kingdom ............... 9122622
Jun. 15, 1992 [GB] United Kingdom ............... 9212650

[51] Int. Cl.$^6$ ................... G08B 17/00; G08B 17/117
[52] U.S. Cl. ................... 340/540; 340/577; 340/595; 340/598
[58] Field of Search .................. 340/579, 577, 340/595, 598, 540

[56] References Cited

U.S. PATENT DOCUMENTS

| 4,090,177 | 5/1978 | Urata et al. | 340/577 |
| 4,319,229 | 3/1982 | Kirkor | 340/577 |
| 4,640,628 | 2/1987 | Seki et al. | 340/577 |

*Primary Examiner*—Glen R. Swann
*Attorney, Agent, or Firm*—James B. Middleton

[57] ABSTRACT

A fire detector, for connection in a fire protection/alarm system, comprises an array of sensors, or a single sensor, of the semiconductor resistor type impregnated with a noble metal. The detector is responsive, by way of a decrease in its resistance, to an increase in any one or more parameters indicative of a fire, namely the atmospheric concentrations of carbon monoxide, hydrogen and water vapor, and temperature, so that a fire is detected regardless of which of these indicators is present. The sensor responds to all of the parameters, and the output signal simultaneously represents changes in all the parameters.

8 Claims, 3 Drawing Sheets

SEMICONDUCTOR SENSORS AND METHOD FOR DETECTING FIRES USING SUCH SENSORS

CROSS-REFERENCE TO RELATED APPLICATION

This application is a continuation in part of the application by the same inventors, filed as PCT/GB92/01964, Oct. 26, 1992, and having the application Ser. No. 08/232,017 now abandoned.

BACKGROUND OF THE INVENTION

1. Field of the Invention

This invention relates to fire detectors of the kind having transducer means, and capable of giving a reaction at ambient temperatures to changes in an atmospheric condition characteristic of the presence of combustion, with the transducer means being arranged to give an electrical output signal representing its response to the said changes. Such a fire detector will be referred to as a fire detector of the kind specified.

2. Discussion of the Prior Art

Commercially available fire detectors generally rely on purely physical principles, by detecting smoke particles or a significant increase in atmospheric temperature, or alternatively, to a lesser extent, by sensing heat or infra-red radiation generated by a fire. Common difficulties with such devices arise from spurious effects, e.g. presence of dust particles or heat emanating from sources other than a fire etc., all of which can lead to false alarms.

It is also known that a fire can be detected in some (though not all) cases by detection of gases produced by the combustion involved, and that this can often afford a means of obtaining very early warning. Studies to demonstrate this are described in the papers of Fardell et al., Fire and Materials, 10 (1986) p. 21–8, Hurst et al., Fire and Materials, 9 (1985) p. 1–8, and Harkoma et al., Combust. Sci. and Tech., 62 (1988), p. 21–9. It has been demonstrated specifically that carbon monoxide sensors can be used to detect fires, as described in Harwood et al., Fire Safety Journal 17 (1991) p. 431–443. In this last-mentioned paper, the sensors are of the impregnated semiconductor type which react to a change in the concentration of carbon monoxide in the atmosphere by a change in their electrical resistance.

Again, it is known that the incidence of false alarms can be reduced, and the security of detecting a fire improved, by using a combination of sensors of different types either in an array, or in single sensors of different type disposed around a building.

A fire variously produces gases (particularly carbon monoxide, and also, commonly, hydrogen), and smoke. Water vapor is often produced by combustion of hydrogenous matter such as hydrocarbons. In addition, of course, there will usually be an increase in atmospheric temperature. The extent to which any one of these factors is present to any significant, or easily-detectable, extent will vary according to the circumstances. This is especially so in the very early stages of a fire when, of course, it is most desirable that the fire be detected: the factor that is predominant at that time should be detected regardless of which factor it happens to be.

Sensors of the impregnated semiconductor resistor type for sensing changes in carbon monoxide (CO) concentration are essentially chemical in function, albeit producing a physical effect in the form of an electrical signal representing the resistance of the sensor. It is known to be desirable to be able to diagnose a fire chemically, using sensors with suitable characteristics, with a view to avoiding the disadvantages of fire detectors that rely on purely physical principles as mentioned above.

The characteristics which are important for fire sensors employing chemical principles include robustness against poisons in the air, sensitivity to gases given off in typical fires, very low power consumption, small size and low cost. While some of these characteristics are present in the general type of sensor described in the above-mentioned paper of Harwood et al., the known art of fire detection using such a sensor still envisages a sensor dedicated to the detection of a single effect characteristic of combustion, e.g. CO concentration. To detect any other effect (such as temperature), it has been thought that separate sensing means would be essential.

Sensors (transducer elements, semiconductor resistors) of porous tin dioxide ($SnO_2$), impregnated with at least one noble metal deposited on the surface of its pores and capable of giving a reaction at ambient temperatures to changes in the concentrations of particular gases in the atmosphere, and methods of making them, are described in the British patent specifications GB 2 249 179A and GB 2 248 306A.

In the first of those documents, a tin dioxide sensor element is impregnated with platinum and an additive which increases its selective sensitivity to the presence of atmospheric hydrogen, by increasing its density. In GB 2 248 306A, a tin dioxide resistor for use as a transducer or sensor element is impregnated with at least one phase of a metal such that the electrical resistance of the sensor is a function of the concentration of a given gas in the atmosphere in such a way that its sensitivity to that gas in trace quantities is reduced, but its sensitivity to the same gas is not impaired at the higher concentrations at which the sensor is most useful.

SUMMARY OF THE INVENTION

An object of the present invention is to provide a fire detector of the kind specified which has all the characteristics mentioned above for sensor using chemical principles, and which, in addition, is able to detect a fire without relying on any one effect of combustion.

Another object is to achieve this with a single transducer means.

According to the invention in the first aspect, a fire detector of the kind specified is characterized in that the transducer means is such as to give a simultaneous response to changes in a plurality of atmospheric conditions characteristic of the presence of combustion, whereby its output signal represents all of the said changes.

In particular, the transducer means is such that its said simultaneous response is to an increase, in the atmosphere, of at least: carbon monoxide concentration; water content; and temperature.

According to a preferred feature of the invention, in such a fire detector the transducer means consists of a single semiconductor resistor, which is preferably also responsive to an increase in hydrogen concentration in the atmosphere. In this connection we have found, surprisingly, that by careful optimization of the manufacturing process, a semiconductor resistor impregnated with noble metal can be produced in which the electrical resistance decreases in response to any one or more of the following:

increase in carbon monoxide concentration above the normal atmospheric background;

a similar increase in hydrogen concentration;

increase in the water vapor content of the atmosphere; and increase in temperature.

Such a sensor responds unambiguously to these indicators, so that it is in effect a plurality of sensors of different combustion effects combined in a single element. Since its response to every one of these effects is a reduction in its resistance, any decrease in resistance can be taken as a reliable indication that a fire is likely to be present.

According to the invention in a second aspect, a method of detecting fire using a transducer means comprising a sensor of semiconductor material impregnated with at least one noble metal and capable of giving a reaction at ambient temperatures to changes in an atmospheric condition characteristic of the presence of combustion, the method including receiving and processing the output signal from the transducer means to produce an alarm signal representing its response to the said changes, is characterised in that it includes receiving and processing the output signal simultaneously representing changes in a plurality of conditions characteristic of the presence of combustion.

BRIEF DESCRIPTION OF THE DRAWINGS

An example of a fire detector in a preferred form according to the invention will now be described with reference to the accompanying drawings.

DETAILED DESCRIPTION OF THE EMBODIMENTS

Figure 1:
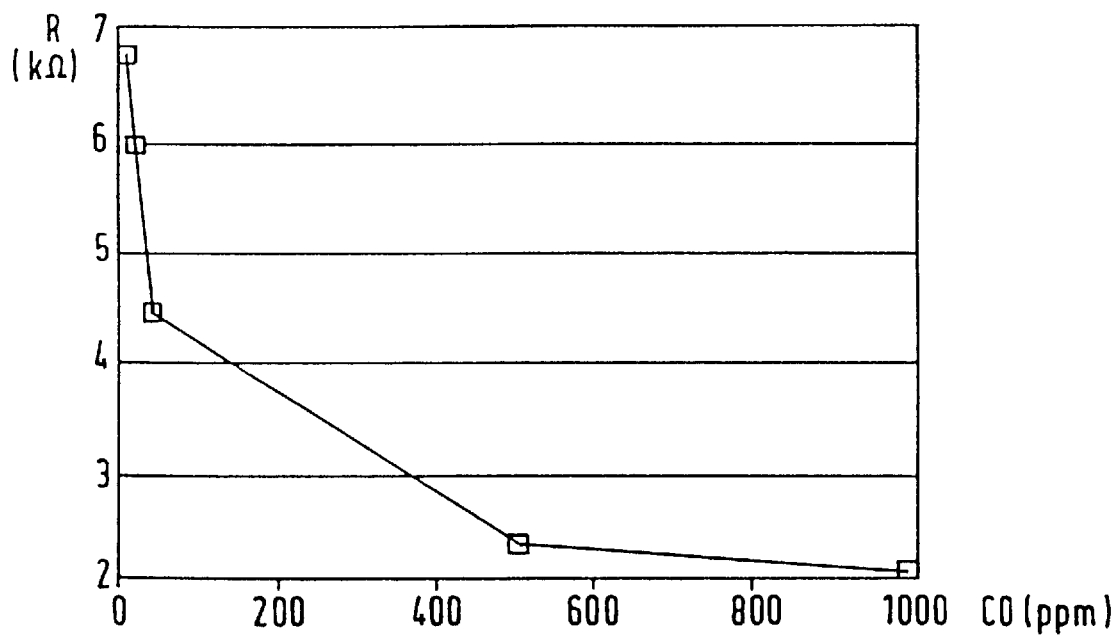
FIG. 1 is a graph showing a typical characteristic curve for resistance of the sensor with atmospheric concentration of carbon monoxide.

The fire detector in this example is part of a fire protection system comprising one fire detector, or a number of fire detectors (all of which may be substantially identical) located in suitable positions in or on a building or other fixed structure. The system may equally be installed in a shop, aircraft or other vehicle.

The system typically includes, in the usual way, a power supply and suitable signal processing means for receiving electrical output signals from the detector, or from each of the detectors, and for processing those signals so as to produce an alarm signal in response to these output signals. The alarm signal is produced when a fire detector gives an output signal indicating that combustion is present, and typically consists of one or more audible and/or visual signals, with or without other functions such as causing fire doors to close automatically, activating a sprinkler system, and so on.

The fire detector itself consists of a single transducer element exposed to the atmosphere and suitably mounted, e.g. on an insulating substrate within a protective housing, with an electrical connection to the signal processor whereby a voltage is applied to the transducer. The transducer element (referred to from here on as the sensor) is a semiconductor resistor, or porous semiconductor material ($SnO_2$ in this example) having at least one noble metal, such as Platinum (Pt) or Palladium (Pd), impregnated into it so as to be deposited on the surface of its pores.

In general terms the sensor is one that is capable of giving a reaction at ambient temperatures, typically in the range of 3°–50° C., though it should also be capable of giving a reaction at the higher temperature to be expected in the presence of a fire. The reaction referred to above is a reaction to changes in atmospheric condition characteristic of the presence of combustion, and consists in a reduction in the electrical resistance of the sensor so that the electrical output signal from the sensor is manifested as a increase in current through the sensor, received and processed accordingly by the processor.

In this example the sensor is so made that it reacts in this way to an increase in any one or more of at least three parameters indicating that combustion is likely to be present, namely:

concentration of CO in the atmosphere;

relative humidity (water vapor concentration in the atmosphere);

temperature; and preferably also the concentration of $H_2$ in the atmosphere.

The processor is preferably programmed in such a way as to ignore output signals from the detector resulting from increases in these parameters due to the variations which are to be expected under normal conditions in the environment being protected by the system. Thus, for example it might be so arranged that the alarm signal is not initiated when:

(a) there is an increase in only one of the parameters, this remaining below a predetermined threshold value; or (b) the initial rate of change of one of the parameter is below a predetermined threshold value, there being no increase in the other parameters above respective predetermined threshold values;

but, that the alarm signal is initiated under all other circumstances. The appropriate threshold values will be chosen accordingly. It will be understood that the processor can of course be programmed in any other desired way, using known techniques.

The sensitivity of the sensor to each of the detectable parameters, and other characteristics of the sensor, will be determined during the manufacturing process, for example by appropriate addition of additives or by use of an additional heat treatment step. The sensor may for instance be of any of the kinds described in the above-mentioned documents GB 2 249 179A, and GB 2 248 306A, to the extent that it is sensitive, to the required degree, to each of the parameters in which increases are to be detected.

Gas sensors employing porous tin oxide bodies or thick films can be made by dispersing a metallic phase on the surface of the pores of the body. It is also well known that fired tin oxide pellets that include finely dispersed platinum make an effective qualitative and quantitative sensing means for both carbon monoxide and hydrogen, and while such a dual response is suitable for certain gas sensing requirements, in fire detectors it is desirable to be able to alter the sensitivity of the sensor to these two gases. Some porosity is always essential in sensor pellets, and relatively high porosity results in sensitivity to both CO and $H_2$; while a decrease in porosity, i.e. an increase in density, tends towards a progressive suppression of sensitivity to Co, until at relatively high density, there remains a sensitivity primarily to $H_2$.

According to established practice, $SnO_2$/Pt pellets are prepared essentially by compression in a die of $SnO_2$ powders, either dry or slightly moistened with water, and are then fired at elevated temperatures. Platinum in introduced by known methods, with final vacuum-deposition of electrodes on the pellet. The pellets so produced are of low density, with a porosity in the region of 50%.

In order to produce elements of greater density, the following methods are suitable, either used separately or in combination with each other:

(a) Minute quantities of "firing fluxes", such as feldspar or bentonite, are intimately mixed with the $SnO_2$ powders to act as densifiers in the ultimate firing process. The quantities of such additives have to be lower in order to avoid the risk of contamination and consequent "poisoning" of the sensitivity of the element to the gas or gases in question. The additives are chosen to have softening points below or in the region of the firing temperature. The effect on density depends on the amount of flux incorporated, and typical flux contents may vary between 0.05% and 0.2%.

(b) Other methods that aim to avoid the danger of contamination consist in mixing a small quantity, e.g. 0.1% to 0.5% by weight, of a temporary binder, such as gum tragacanth, into the $SnO_2$ moulding powder with water and repeatedly kneading the resulting dough, followed by partial drying and straining through a coarse sieve to produce a granular powder for moulding.

The temporary binder is removed again in the firing process, promoting formation of a pellet of increased density. The degree of density can be regulated by varying the binder content and water content of the moulding powder.

In either method (a) or (b), care has to be taken not to exceed the optimum density, which would result in difficulty in the Pt dispersion procedure and in impaired gas sensitivity.

The response characteristics of the sensor over particular gas concentration ranges can also be predetermined by the use of more than one metallic element in the dispersed phase on the surface of the pores. The additional phase or phases modifying the surface of the pores of the sending element, which is typically 50% dense, comprise fine particles produced from mixed metal salts, which are dispersed in the porous tin oxide body and then co-precipitated and decomposed in a manner which is otherwise generally similar to established methods of production. The final step in the dispersion of the metallic phase can be achieved by a heat treatment such as to obtain thermal decomposition of the co-precipitated salts. This is carried out at temperatures low enough, and over periods of time short enough, to avoid solid solution reactions between the tin oxide and metallic phases such as to give rise to the formation of unwanted further phases damaging to the gas response.

The above procedure can be used in order to deposit a single phase, such as platinum, on the surface of the pores of the sending element. In this case the salt is precipitated, rather than co-precipitated, prior to heat treatment. An example of a suitable time and temperature regime, in the case where the metallic phase consists only of platinum, is 350° C. for one hour.

For some purposes where a particular target gas is to be detected, for example in the detection of carbon monoxide present as a result of the early stages of a fire which it is desired to detect before it becomes a conflagration, sensitivity is required at very low concentrations of the target gas.

The response of sensors of the kind described above, when they are operating as resistors sensitive to carbon monoxide without being heated (i.e. working at ambient temperature, typically in the range 3°–35° C.) can be inhibited by relatively high concentrations of organic vapors that may be present in the surrounding atmosphere. Examples of such vapors are acetic acid, methylated spirit and silicon-containing organic molecules. Additionally, these sensors exhibit long response times, typically many minutes, and their sensitivity is poor when expressed as a fractional change in resistance for a given change in gas concentration. This effect can be overcome by the incorporation of an activated carbon filter in the gas path between the sensor element and the surrounding atmosphere.

When the sensor is heat-treated at a temperature lower than the original decomposition temperature of the precipitated or co-precipitated salts, its electrical resistance increases. Its response to carbon monoxide is enhanced, and its speed of reaction to a step-function change in carbon monoxide concentration is greatly increased, as compared with the rate of response of the sensor after the first heat treatment previously described.

One method of making a porous tin dioxide gas sensor includes the steps of:

dispersing at least one metal salt in the porous tin oxide body of the sensor;

precipitating or co-precipitating the salt or salts;

applying a first heat treatment to obtain thermal decomposition of the precipitated or co-precipitated salts, whereby to deposit fine metallic particles on the surface of the pores of the body; and, applying a second heat treatment at a temperature lower than that of the first heat treatment, whereby to increase the electrical resistance of the sensor.

Further investigation reveals that, over and above variables in the method already established for dispersing the precipitated salt or salts within the pores of the sensing element, the precise nature of the first heat treatment has a substantial bearing on the magnitude and speed of response of the sensor, particularly in relation to its responses to the presence of carbon monoxide.

When the sensor comprises a porous tin oxide body in which the surface of the pores are dotted with multiple metallic dispersions, the nature of the second heat treatment substantially determines the extent and rate of the response of the sensor, particularly to carbon monoxide.

The sensor response can be inhibited through coming into contact with molecules in the atmosphere other than those to which the sensor is intended to respond. As the sensor response is inhibited, its resistance in the air will drift (typically to lower values), while the change in its resistance when exposed to a step-function change in concentration of the test gas becomes smaller. In extreme cases of response inhibition this resistance change can become negligible. The second heat treatment is beneficial to the recovery of response capability under these circumstances.

It will be understood that the metallic dispersion in the pores may be of platinum alone, platinum with other metallic elements, or other suitable combinations of elements.

Since heat treatment follows the decomposition of the precipitate in the pores, it can be accomplished during a single heat treatment cycle comprising the first and second heat treatment steps in successions. Alternatively the second heat treatment step may constitute a separate cycle, as in response recovery. This is at a lower temperature than the first or decomposition heat treatment step, but can be performed over a shorter or longer time, depending on the combination of properties required, for example resistance, response speed, response magnitude.

FIGS. 1 to 6 illustrate the behavior of a typical sensor for a fire detector according to the invention. The quantity "ppm" in FIGS. 1 and 6 means parts per million.

Sensors whose characteristics are depicted in the figures were typically prepared by screen printing. Metastannic acid of a nominally pure, commercial grade was mixed with antimony oxide (0.2–0.3 wt %) and calcined at 1000° C. for 8 hours to form an antimony doped tin oxide powder of small primary crystallite size. This powder was ground to a smooth paste with a solution of a platinum complex to give a final Pt content of 0.05–0.1 wt %. The powder was then dried, and the dried powder was mixed with a commercial screen printing vehicle (cellulose acetate in terpinol) to give a thick fluid, which was then screen-printed in layers 10–15 micrometers thick over gold electrodes on an alumina substrate. The resulting printed sensors were dried, and then fired for 1 hour at 600° C. in a mildly reducing atmosphere. This caused the platinum complex to be decomposed so as to deposit a highly active fine particle dispersion of Pt over the tin dioxide pore surface.

Figure 2:
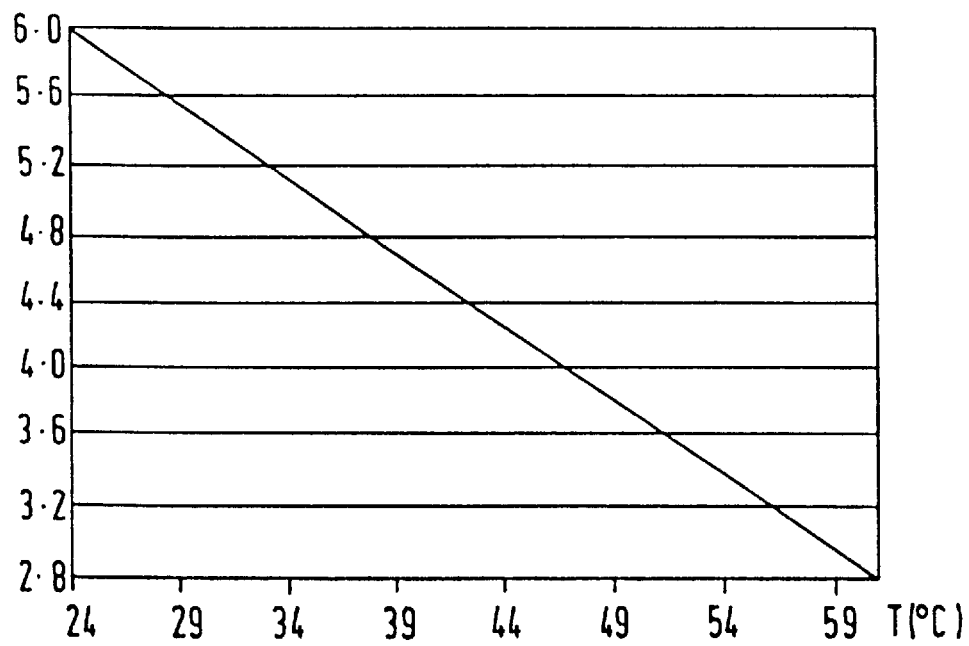
FIG. 2 is a graph showing a typical characteristic curve for variation of the resistance of the sensor with atmospheric temperature.

FIG. 1 shows how its resistance R decreases with increasing CO concentration in dry air, while FIG. 2 is a characteristic curve showing how R varies with temperature T.

Figure 3:
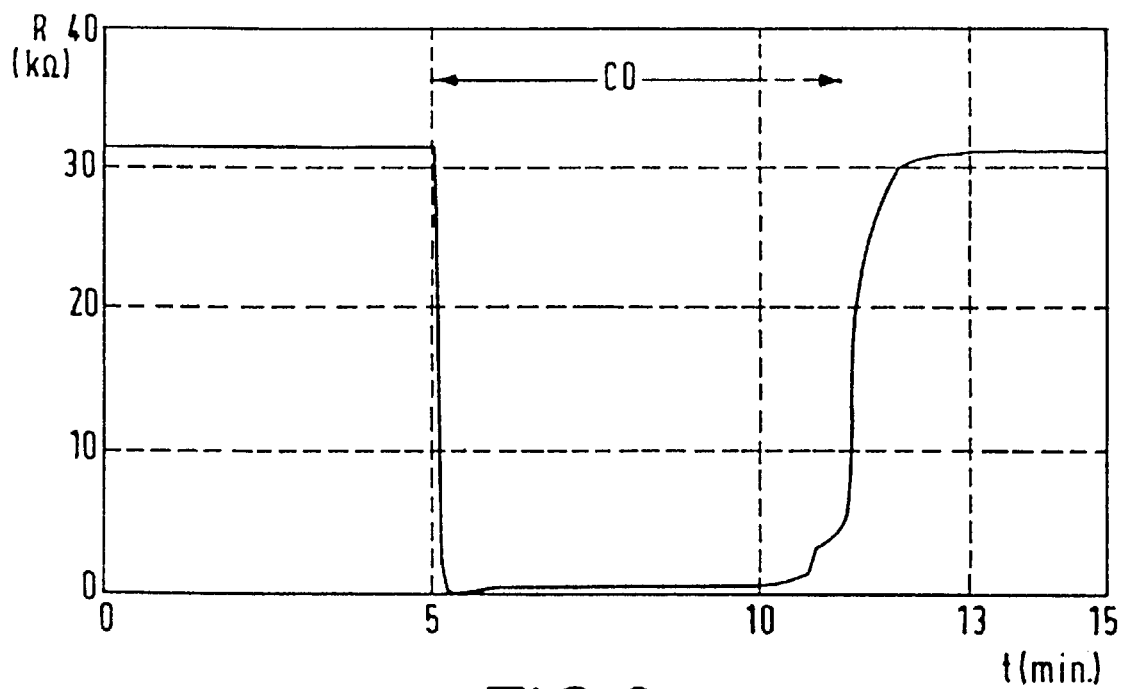
FIGS. 3 and 4 are diagrams of resistance plotted against time, showing reduction in the resistance of the sensor on introduction to carbon moxoxide and hydrogen respectively.
Figure 4:
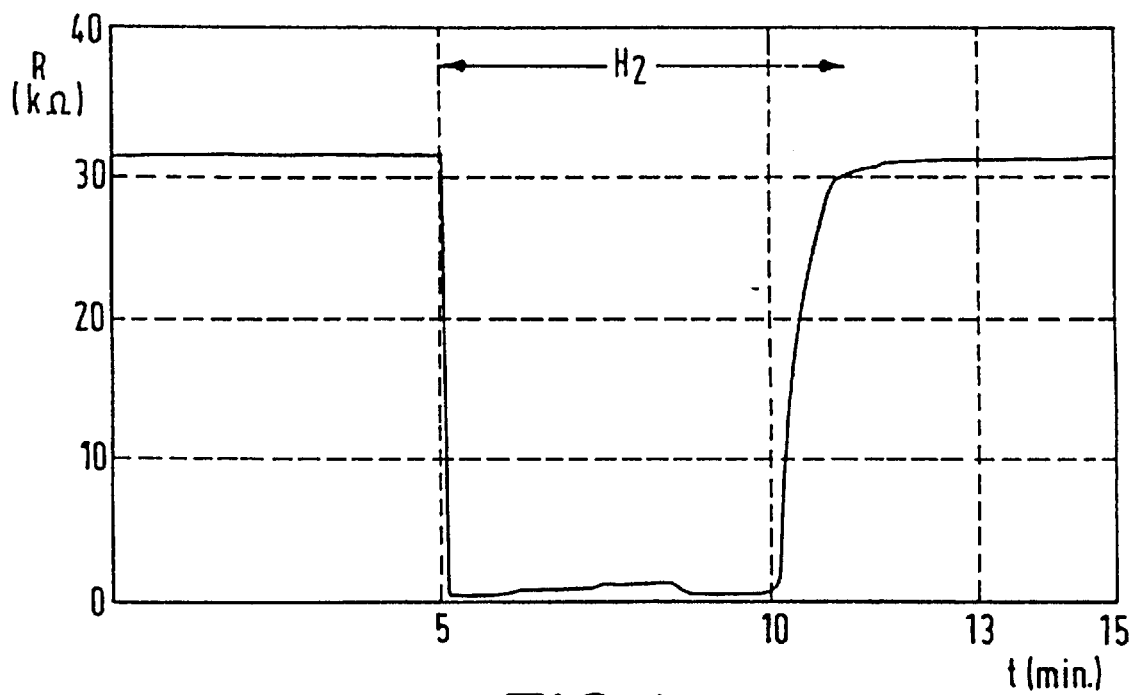

FIGS. 3 and 4 show how R varied over a period of time t in two experiments in which, at 5 minutes, CO and $H_2$ respectively were rapidly introduced into an air atmosphere, being flushed away rapidly starting at 10 minutes. The concentration of each gas was 1%.

Figure 5:
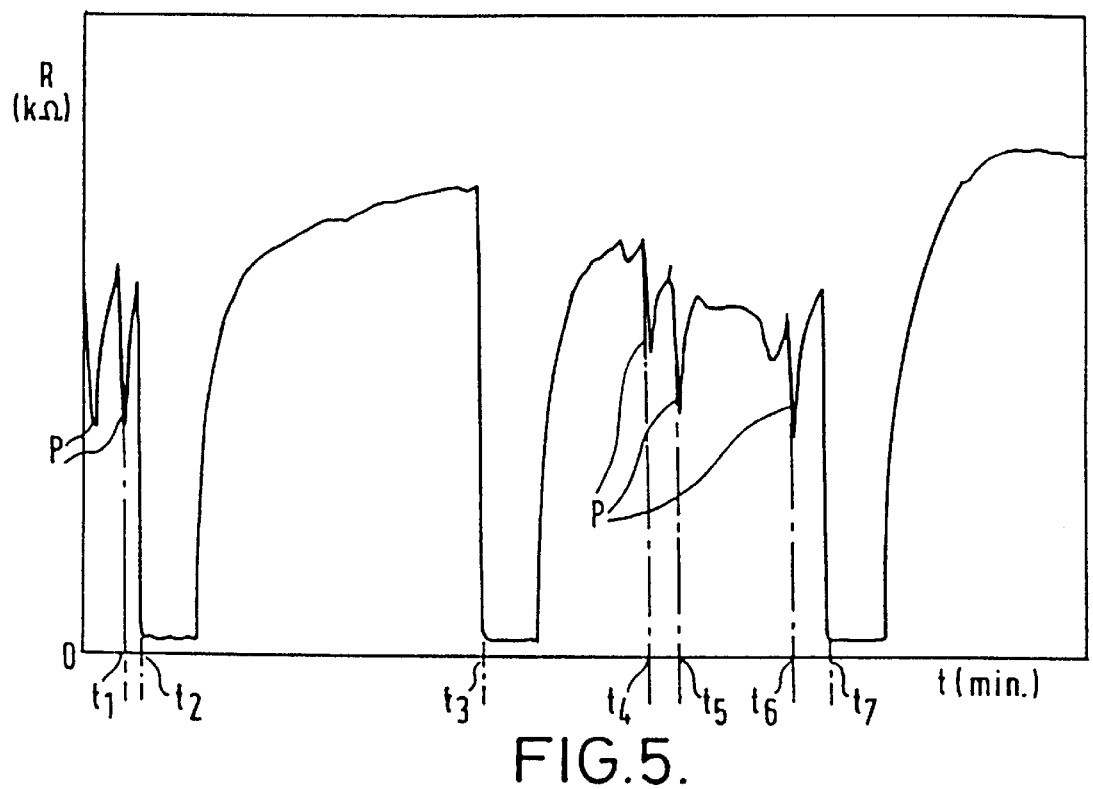
FIG. 5 is a diagram of resistance plotted against time, showing the effect on the former of the occurrence of short introductions of water vapor into the atmosphere.

FIG. 5 shows the curve of variation in R with time t during an experiment in an atmosphere consisting of air at 15% relative humidity. A 1% concentration of CO was introduced rapidly at times $t_1$, $t_2$, $t_4$, $t_5$ and $t_6$. The resulting brief decreases in R showed in the pulses indicated at P.

It will be seen from FIGS. 1 to 5 that the resistance of the sensor is significantly reduced very rapidly in response to an increase in any one of the four detected parameters, independently of any of the others. Accordingly, if more than one parameter increases, the reduction in resistance is cumulative, i.e. the output signal is enhanced, so that an increase in any parameter cannot tend to cancel the effect due to an increase in any other parameter. Consequently the sensor is a reliable means for detecting the possibility of fire in response to any or all of the parameters discussed.

Figure 6:
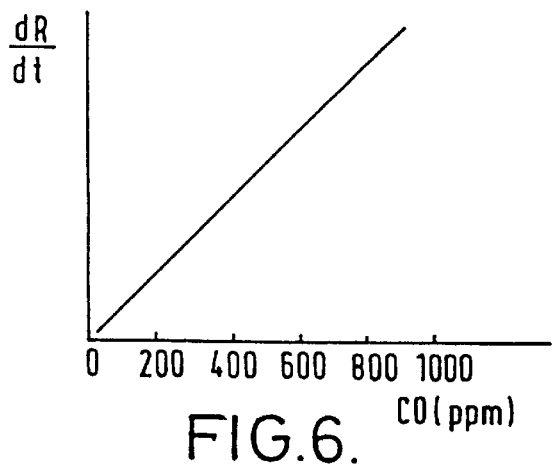
FIG. 6 is a graph showing the effect of carbon monoxide on the rate of change of resistance of the sensor, in particular in regard to the initial response rate of the latter.

In FIG. 6, CO was introduced into an air atmosphere and the rate of change (rate of decrease) dR/dt of resistance with time was measured and plotted against the concentration of CO. It will be observed that the rate of change of the resistance is proportional to the concentration of CO in the air. This fact can be used by the processor, using known techniques, to enable the processor to distinguish genuine fire warning signals from spurious or transient signals, or for any other appropriate purpose.

Figure 7:
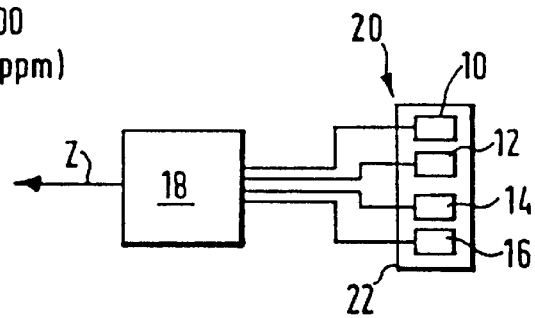
FIG. 7 shows diagrammatically a fire detector according to the invention in which the transducer means is in the form of an array of sensors.

The detector preferably comprises a single sensor as described above. However, within the scope of the invention it may comprise an array consisting of a number of individual sensors, each dedicated primarily (though not necessarily exclusively) to the sensing of a specific one of the parameters which are to be detected. Thus such an array consists, for example and as shown in FIG. 7, of a gas sensor 10 for detecting changes in CO concentration, together with a heat sensor 12 for detecting temperature changes, and/or a humidity sensor 14.

The heat sensor, reacting to increases in temperature due to a fire, provides corroboration of the signals from the gas and humidity sensors. In addition, it permits correction of, or allowance to be made for, a pre-determined extent of cross-sensitivity to heat rises by the gas sensor. Such cross-sensitivity, being an essentially constant factor in any particular type of gas sensor, can be readily pre-established by calibration.

The humidity sensor likewise provides corroboration for the signals of the gas and heat sensors by detecting the humidity increases associated with a fire, while again allowing compensation to be made for the pre-determined cross-sensitivity of the gas sensor to humidity.

An array 20 comprising at least one such gas sensors element 10 (FIG. 7), together with at least one, or preferably both, of the heat and humidity sensors 12, 14, is connected to the signal processing means 18, which is arranged so as to initiate the alarm signal 2 only when the output signal from the gas sensor 10 is corroborated and corrected where necessary from cross-sensitivity, by the heat sensor 12 and/or the humidity sensor 14. The extent of cross-sensitivities to both temperature and humidity is low in the preferred types of gas sensor described, in relation to the response to gaseous emanations, in particular those of CO. A further gas sensor 16, responsive to hydrogen concentration, may of course be included in the array.

Some of the preferred types of sensor elements in a fire detector according to the invention will now be more specifically described.

The CO sensor 10 is preferably of the type based on $SnO_2$ impregnated with Pt or Pd, including devices of the general type described in the document GB 2 249 179A. Such sensors can be produced so as to exhibit high sensitivity to CO with relatively low cross-sensitivity to moisture and heat, and in this embodiment they are of the kind operable at ambient temperatures in the manner discussed earlier herein.

Different types of heat sensors 12 can be used, preferred elements being those based on electrical resistors with numerically high temperature coefficients of resistance, including those known by the Trademark "THERMISTOR". Examples of preferred types are based on resistor bodies of oxide ceramics, e.g. having a spinel crystal structure. Other such resistors are based on SiC, Pt, etc.

Various conventional types of humidity sensors 14 may be used. Preferred types are those relying either on changes in resistance or capacitance in response to humidity effects in resistors or capacitors, e.g. with porous titanate ceramic dielectrics respectively.

The single sensor, or the sensors in array, of a fire detector according to the invention may be deposited or otherwise carried upon a mother plate 22, being for example silk-screen printed on a ceramic, e.g. alumina substrate.

Relatively inexpensive fire detectors can thus be produced, which are substantially less prone to false alarms than is possible in conventional systems. An additional advantage is that fire detectors according to the invention preferably comprise elements all of which are unheated, and which thus require very low power supplies.

I claim:

1. In a fire detector having transducer means comprising a sensor of semiconductor material impregnated with at least one noble metal, and capable of giving a reaction at ambient temperatures to changes in an atmospheric condition characteristic of the presence of combustion, said transducer means being arranged to give an electrical output signal representing its response to the said changes in an atmospheric condition, the improvement wherein said transducer means is such as to give a simultaneous response to changes in a plurality of atmospheric conditions characteristic of the presence of combustion, whereby its output signal represents all of the said changes.

2. In a fire detector according to claim 1 in which the said reaction consists in changes in the electrical resistance of the sensors, the further improvement wherein said transducer means is such that its said simultaneous response is to an increase in the atmosphere of at least carbon monoxide concentration, water content, and temperature.

3. In a fire detector according to claim 2, the improvement wherein said transducer means consists of a single semiconductor resistor.

4. In a fire detector according to claim 3, the improvement wherein said single resistor is further responsive to an increase in the atmosphere of hydrogen concentration.

5. In a fire detector according to claim 1, the further improvement wherein said transducer means consists of an array, said array comprising at least a gas sensor and a heat sensor.

6. In a fire detector according to claim 1, the improvement wherein said transducer means comprises an array including at least a gas sensor and a humidity sensor.

7. In a method of detecting a fire, using a transducer means comprising a sensor of semiconductor material impregnated with at least one noble metal and capable of giving a reaction at ambient temperatures to changes in an atmospheric condition characteristic of the presence of combustion, said method including the steps of receiving and processing the output signal from the transducer means to produce an alarm signal representing its response to the said changes, the improvement wherein said step of receiving and processing the output signal simultaneously represents changes in a plurality of conditions characteristic of the presence of combustion.

8. In a method according to claim 7, the improvement comprising using a single semiconductor resistor constituting said transducer means, the said output signal representing atmospheric increases in carbon monoxide concentration, hydrogen concentration, water vapor content, and temperature.

\* \* \* \* \*